Figure 1:
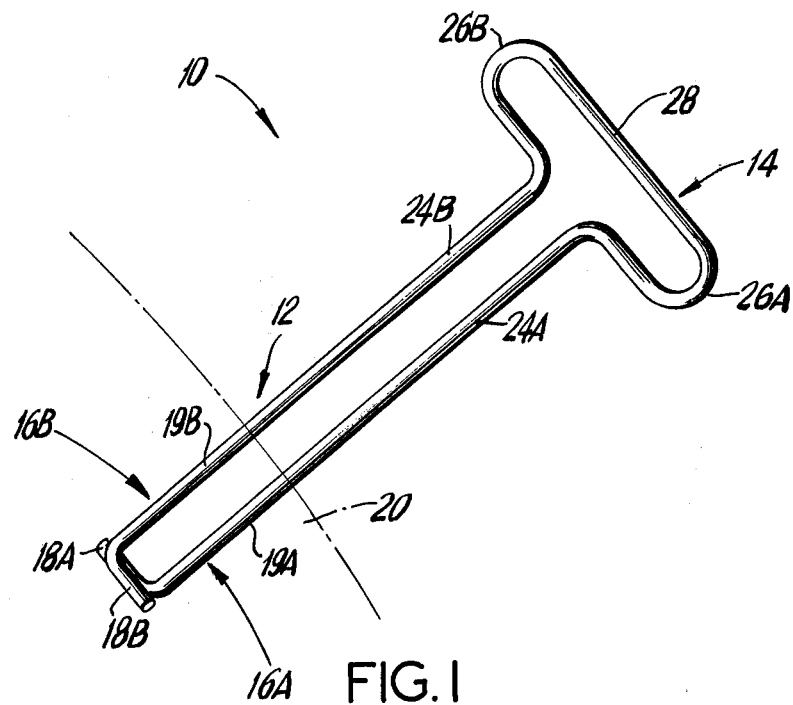

United States Patent [19]

Fisher

[11] 4,026,023
[45] May 31, 1977

[54] CLOSED FLAP SPRING FOR ORTHODONTIC APPLIANCES

[76] Inventor: Robert Leon Fisher, 108 E. 38th St., New York, N.Y. 10016

[22] Filed: Nov. 26, 1975

[21] Appl. No.: 635,153

[52] U.S. Cl. ............................................. 32/14 E
[51] Int. Cl.² ......................................... A61C 7/00
[58] Field of Search ........................ 32/14 E, 14 A

[56] References Cited

UNITED STATES PATENTS 360,695   4/1887   Holmes ............................. 32/14 E

FOREIGN PATENTS OR APPLICATIONS 972,790   10/1964   United Kingdom ............... 32/14 E

*Primary Examiner*—Robert Peshock

[57] ABSTRACT

An improved closed flap spring for orthodontic appliances used in orthodontic treatment of a patient, including a wire fashioned in the shape of a T, having a vertical portion and a horizontal portion, the vertical portion having a pair of spaced tag portions at its lower end for processing or attaching to the orthodontic appliance, a pair of spaced parallel arm portions as extensions of the tag portions forming the upper end of the vertical portion of the T, a pair of rounded loop portions, one of the loop portions extending generally horizontally outward from one of the arm portions in one direction and the other loop portion extending generally horizontally outward from the other arm portion in the opposite direction, and a bridge portion interconnecting the loop portions, the loop portions and bridge portion forming the horizontal portion of the T, which horizontal portion is free to engage and control the directional movement of a tooth.

14 Claims, 2 Drawing Figures

CLOSED FLAP SPRING FOR ORTHODONTIC APPLIANCES

The present invention relates to devices for orthodontic treatment of a patient, and more particularly to an improved closed flap spring for use in orthodontic appliances used in orthodontic treatment of a patient.

Springs are well known for processing or attachment to orthodontic appliances used in orthodontic treatment. These springs generally include two types:

1. Open springs; and
2. Closed springs.

Open springs may be fabricated in various shapes, e.g., S and W. However, open springs have the disadvantage of being quite flexible, thereby being easily distorted prior to or during use, as well as often not exerting sufficient force on the desired tooth to obtain the required corrective movement or in some cases actually causing incorrect movement.

In contrast, closed springs or flap springs are generally more rigid. However, known closed spring configurations also suffer from certain inadequacies. Among other inadequacies, the known closed spring configurations generally have too short a lever arm and are thus more rigid, thereby limiting the degree of manipulation and versatility, or have too long a lever arm and are thus quite flexible. An example of a closed spring which is quite rigid is a closed spring having criss-crossing arms extending between the free or tooth engaging end of the closed spring and the tag portions which are processed to the orthodontic appliance. An example of a closed spring which is quite flexible is a closed spring having elongate lever arms bent generally at right angles to the tag portions and with a single asymmetric rectangular loop at the free end.

It is an object of the present invention to provide a closed flap spring for use in orthodontic appliances which has not only sufficient rigidity and sufficient flexibility but also sufficient versatility to properly control tooth movement while at the same time being easily manipulated to provide power engagement with the tooth or teeth whose movements are to be controlled.

It is a further object of the present invention to provide a closed flap spring for use in orthodontic appliances which is capable of providing improved controlled directional tooth movement over a longer period of time than with prior art springs.

It is a further object of the present invention to provide a closed flap spring for use in orthodontic appliances which is particularly advantageous in imparting rotational movement to a tooth.

It is a further object of the present invention to provide a closed flap spring for use in orthodontic appliances which when coupled with another orthodontic attachment or sometimes without being coupled with another orthodontic attachment is particularly advantageous in imparting torquing movement to a tooth.

It is a still further object of the present invention to provide a closed flap spring which, because it is uniquely shaped to minimize stress points, is less subject to fracture, thereby increasing the longevity and safety of the spring and the orthodontic appliance to which it is processed or attached.

Other objects, aspects and advantages of the present invention will be apparent from the detailed description and the accompanying drawings.

Briefly, the present invention includes an improved closed flap spring for use in orthodontic appliances used in orthodontic treatment of a patient, including a wire fashioned in the shape of a T having a vertical portion and a horizontal portion, the vertical portion having a pair of spaced tag portions at its lower end for attaching to the orthodontic appliance, a pair of spaced parallel arm portions as extensions of the tag portions forming the upper end of the vertical portion of the T, a pair of rounded loop portions, one of the rounded loop portions extending generally horizontally outward from one of the arm portions in one direction and the other rounded loop portion extending generally horizontally outward from the other arm portion in the opposite direction, and a bridge portion interconnecting the rounded loop portions, the rounded loop portions and bridge portion forming the horizontal portion of the T, which horizontal portion is free to engage and control the directional movement of a tooth or teeth.

Figure 2:
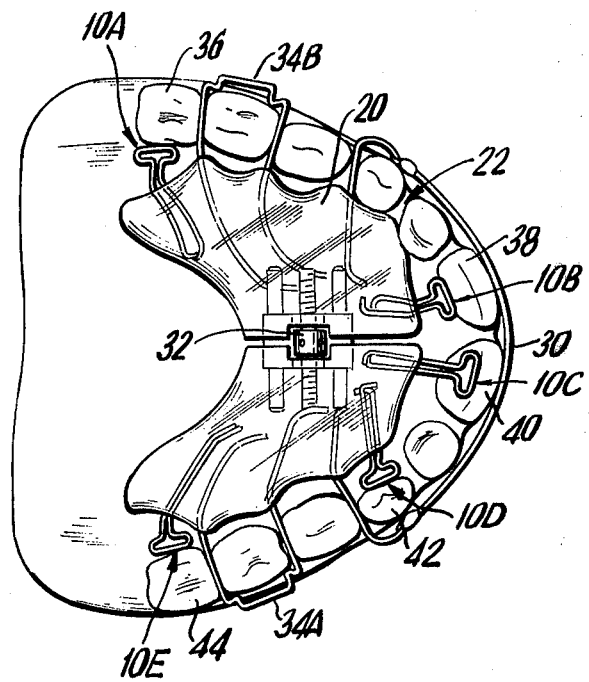

The preferred embodiment of the present invention is illustrated in the drawings. However, it should be understood that the present invention should not be limited solely to the preferred embodiment. The drawings are as follows:

FIG. 1 is an enlarged perspective view of a closed flap spring in accordance with the present invention; and FIG. 2 is a plane view of an orthodontic appliance including a plurality of flap springs seated in the mouth of a patient.

Referring to FIG. 1, a closed flap spring in accordance with the present invention is generaly illustrated at 10. The flap spring 10 fashioned in the shape of a T from a single piece of wire has a vertical portion 12 and horizontal portion 14. The vertical portion 12 includes a pair of spaced tag portions 16A and 16B at its lower end. Advantageously, the ends 18A and 18B of the tag portions 16A and 16B are bent inwardly toward one another generally at rounded right angles to the non-bent portions 19A and 19B of the tag portions 16A and 16B, with one end of 18A or 18B overlying the other end 18B or 18A. The non-bent portions 19A and 19B of the tag portions 16A and B are generally parallel with one another. Preferably the ends 18A and 18B and non-bent portions 19A and 19B are embedded in an acrylic plate 20 of a removable dental appliance 22, seen in FIG. 2. The tag portions 16A and B may be considered to terminate at the points of attachment or in the case where the tag portions are embedded in an acrylic plate 20, at the points where the wire emerges from the acrylic plate 20. The portions of the wire emerging from the acrylic plate 20 are designated as arm portions 24A and 24B or more aptly a lever arm. The total length of the vertical portion 12 is generally constant with the individual length of the tag portions 16A and 16B and arm portions 24A and 24B varying in accordance with the point of attachment or amount of the vertical portion 12 embedded in an acrylic plate 20. The arm portions 24A and 24B are spaced parallel to one another and are aligned with the axes of the tag portions 16A and 16B. Extending horizontally outward in opposite directions from the remote end of the arm portions 24A and 24B are symmetrical rounded loops 26A and 26B. The rounded loops 26A and 26B are interconnected by a bridge portion 28 to complete the horizontal portion 14 or free end of the T-shaped closed flap spring 10.

Preferably, the T-shaped closed flap spring 10 is made of stainless steel wire having a diameter of .018 inches, or of precious or semiprecious metals which are body compatible and compatible with orthodontic appliances, and which may be readily attached thereto. The orthodontic appliances may be of the permanent or removable type and may include orthodontic archwires as well as acrylic or vulcanite plates to which the T-shaped closed flap spring 10 is processed or attached, e.g., by soldering to an archwire or by embedding in an acrylic or vulcanite plate.

Preferably, the horizontal portion or free end 14 has a length which varies from between about ⅛ inch to about ⅜ inch, depending upon the width of the tooth and the type of controlled movement to be imparted to the tooth by the T-shaped closed flap spring 10, with the rounded loops 26A and 26B having a radius of about 1/32 inch to about 1/16 inch. Preferably, the length of the vertical portion 12 is about ⅜ inch to ½ inch with the length of the arm portions 24A and 24B varying between about 1/16 and ¼ inch, depending upon the location of the tooth to be engaged by the free end 14 and the amount of force which is desired to be exerted on the tooth. Further, the spacing between the tag portion 16B and arm portion 24B and tag portion 16A and arm portion 24A, respectively, is preferably between about 1/32 inch to about 1/16 inch.

Referring to FIG. 2, removable orthodontic appliance 22 is shown including five T-shaped closed flap springs 10A–E. In addition to the T-shaped closed flap springs 10A–E, the orthodontic appliance 22 includes other conventional elements, i.e., an acrylic plate 20, an archwire 30, an arch expansion screw 32, and clasps 34A and 34B. It should be understood that other conventional springs may also be attached to the orthodontic appliance 22 or the type of orthodontic appliance may vary as desired, depending upon the type of orthodontic treatment indicated.

The T-shaped closed flap spring 10A is shown engaging and directing the movement of the tooth 36 buccally. The T-shaped closed flap spring 10B is shown engaging and directing the movement of the tooth 38 labially. The T-shaped closed flap spring 10C is shown engaging and directing the movement by engaging the tooth 40 applying and directing the movement of torque thereto. The T-shaped closed flap spring 10D is engaging the tooth 42 for imparting rotation thereto. The T-shaped closed flap spring 10E is shown engaging and directing the movement of the tooth 44 buccally.

Although the orthodontic appliance 22 is shown with five T-shaped closed flap springs 10A–E, it should be understood that the number of flap springs 10A–E will vary depending on the number of teeth to be orthodontically treated. Moreover, it should further be understood that each T-shaped closed flap spring 10 may be utilized to impart other types of desired directional tooth movement in addition to the particular types of tooth movement shown in FIG. 2. Specifically, in addition to buccal, labial, rotational, and torque movement, the T-shaped flap spring 10 may be used to influence teeth to move lingually, distally, mesially, or, in combination with other attachments, to intrude or extrude teeth.

In providing orthodontic treatment, the orthodontic appliance 22, or any other type of permanent or removable plate or archwire, is fitted within the mouth of a patient in accordance with well established techniques to provide desired directional tooth movement. The individual T-shaped closed flap springs 10 are embedded in the orthodontic split plate 20 or soldered or attached to an archwire or main body wire in a manner similar to the attachment of conventional open and closed springs, depending on the type of plate or wire being used, the location of the teeth, and the type of directional movement to be imparted thereto. In view of the spaced generally parallel tag portions 16A and 16B, the T-shaped closed flap spring 10 may be easily and securely embedded in plate 20 or attached to an archwire or main body wire. Moreover, the exposed length or lever arm of the vertical portion 12 (arm portions 24A and 24B) may be readily adjusted to provide the proper lever arm for influencing the movement of the tooth to be orthodontically treated. Further, the horizontal portion 14 or free end of the T-shaped closed flap spring 10 may be readily bent or shaped by the supplier or practitioner to impart the desired type of controlled movement to the tooth in accordance with the location of the tooth, the resulting movement created by the lever arm and the point or points of contact of the free end of the spring 10 with the tooth.

It should be understood by those skilled in the art that various modifications may be made in the present invention without departing from the spirit and scope thereof, as described in the specification and defined in the appended claims.

What is claimed is:

1. An improved orthodontic appliance for controlling the directional movement of a tooth or teeth, said appliance having at least one closed flap spring with one end affixed and a free end engaging a tooth or teeth to be moved in which the improvement comprises:
    a closed flap spring in the shape of a T, fashioned from a piece of wire, said closed flap spring having a substantially vertical portion and a substantially horizontal portion, the vertical portion having a pair of affixed tag portions at its lower end, a pair of substantially parallel spaced arm portions extending from said tag portions, a pair of rounded loop portions, one of said rounded loop portions extending generally horizontally outward from one of said arm portions in the opposite direction, and a bridge interconnecting said rounded loop portions, and said bridge portion forming said horizontal portion and engaging the tooth or teeth to be moved, such parallel arm portions, said loop portions and said bridge portion applying a controlled movement to said tooth or teeth, said loop portions and said bridge portion cushioning said force applied to said tooth or teeth.

2. The improved orthodontic appliance recited in claim 1, in which the orthodontic appliance includes a removable plate, wherein:
    said tag portions are affixed by embedded said tag portions within the removable plate and said arm portions extend outwardly from the removable plate, the length of said tag portions embedded within the removable plate and therefore the length of said vertical portion extending outwardly from the removable plate varying in accordance with the movement to be imparted to the tooth or teeth.

3. The improved orthodontic appliance recited in claim 2, wherein:
    the length of said arm portions vary between about 1/16 inch to about ¼ inch.

4. The improved orthodontic appliance recited in claim 1, wherein:

the length of said horizontal portion of said T-shaped closed flap spring varies between about ⅛ inch to about ⅜ inch.

5. The improved orthodontic appliance recited in claim 1, wherein:
said loops have a radius between about 1/32 inch to about 1/16 inch.

6. The improved orthodentic appliance recited in claim 1, wherein:
a plurality of said closed T-shaped flap springs are attached to the orthodontic appliance for engaging and controlling the directional movement of certain teeth.

7. The improved orthodontic appliance recited in claim 6, wherein:
one of said tag portions and one of said arm portions are axially aligned and the other of said tag portions is axially aligned with the other of said arm portions.

8. An improved orthodontic appliance for controlling the direction of movement of certain teeth of a patient including a removable plate having a plurality of flap springs with one end of each of the flap springs affixed to said removable plate and another end for engaging and controlling the teeth to be directionally moved, the improvement comprising:
closed flap springs in the general shape of a T, fashioned from a piece of wire, each of said closed flap springs having a pair of affixed tag portions, a pair of parallel arm portions extending outwardly from the tag portions, a pair of rounded loop portions, one of said rounded loop portions extending generally horizontally outward from one of said arm portions in one direction and said other rounded loop portion extending generally horizontally outward from the other of said arm portions in the opposite direction, and a bridge portion interconnecting said rounded loop portions, said rounded loop portions and bridge portion of each of said closed flap springs forming free ends to engage and control the directional movement of certain teeth, said parallel arm portions, said loop portions and said bridge portion applying a controlled directional movement force to said teeth, said loop portions and said bridge portion cushioning said force applied to said teeth.

9. An improved closed flap spring for an appliance used in orthodontic treatment, comprising:
a wire fashioned in the shape of a T, said wire having a vertical portion with a pair of spaced tag portions at its lower end for affixing to the appliance, a pair of substantially parallel arm portions as extensions of the tag portions, a pair of rounded loop portions, one of said rounded loop portions extending outward from one of said arm portions in one direction and the other of said rounded loop portions extending outward from the other of said arm portions in the opposite direction, and a bridge portion interconnecting said rounded loop portions, said rounded loop portions and said bridge portion forming a portion extending substantially transverse to the direction of said arm portions and, being free to engage and control the directional movement of a tooth by cushioning and applying to said tooth the combined forces of said arm portions, said loop portions and said bridge portion.

10. The improved flap spring recited in claim 9, wherein:
said tag portions are adapted to be attached to the appliance with the arm portions extending outwardly from said appliance, the length of the said arm portions varying in accordance with the movement to be imparted to the tooth.

11. The improved flap spring recited in claim 9, wherein:
the length of the said horizontal portion varies between about ⅛ inch and about ⅜ inch.

12. The improved closed flap spring recited in claim 9, wherein:
the length of said arm portions varies between about 1/16 inch and ¼ inch, depending upon the termination of the points of attachment to the dental appliance.

13. The improved closed flap spring recited in claim 12, wherein:
said parallel arm portions are spaced apart a distance of between about 1/32 inch to about 1/16 inch.

14. An improved flap spring for an appliance used in orthodontic treatment, comprising:
a wire fashioned in the shape of a T, said wire having a vertical portion with a pair of spaced tag portions at its lower end for affixing to the orthodontic appliance, a pair of parallel arm portions as extensions of the tag portions at the upper end of the vertical portion of the T, said tag portions being adapted to be attached to the orthodontic appliance with the arm portions extending outwardly from the orthodontic appliance, said parallel arm portions being spaced apart a distance of between about 1/32 inch to about 1/16 inch, a pair of rounded loop portions, one of said rounded loop portions extending outward from one of said arm portions in one direction and the other of said rounded loop portions extending outward from the other of said arm portions in the opposite direction, and a bridge portion interconnecting said rounded loop portions, said rounded loop portions and said bridge portion forming a portion extending substantially transverse to the direction of said arm portions, the length of the said transverse portion varying from between about ⅛ inch to about ⅜ inch and being adapted to engage and control the movement of a tooth or teeth.

* * * * *